United States Patent
Kajihara

(10) Patent No.: US 8,258,467 B2
(45) Date of Patent: Sep. 4, 2012

(54) MASS-ANALYZING METHOD AND MASS SPECTROMETER

(75) Inventor: Shigeki Kajihara, Uji (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/128,389

(22) PCT Filed: Nov. 10, 2008

(86) PCT No.: PCT/JP2008/003246
§ 371 (c)(1),
(2), (4) Date: May 9, 2011

(87) PCT Pub. No.: WO2010/052756
PCT Pub. Date: May 14, 2010

(65) Prior Publication Data
US 2011/0215238 A1    Sep. 8, 2011

(51) Int. Cl.
*H01J 49/40* (2006.01)
(52) U.S. Cl. ......... 250/287; 250/291; 250/281; 250/282
(58) Field of Classification Search ............... 250/287, 250/290, 291, 281, 282
See application file for complete search history.

(56) References Cited

U.S. PATENT DOCUMENTS

| 7,091,480 B2 * | 8/2006 | Yamaguchi et al. | ......... 250/287 |
| 2011/0231109 A1 * | 9/2011 | Furuhashi et al. | ............. 702/24 |

FOREIGN PATENT DOCUMENTS

| JP | 2005-079049 | 3/2005 |
| JP | 2005-116343 | 4/2005 |
| JP | 2006-228435 | 8/2006 |
| JP | 2008-027683 | 2/2008 |

OTHER PUBLICATIONS

Japanese language international preliminary report on patentability dated Jun. 21, 2011 and its English language translation for corresponding PCT application PCT/JP2008/003246.

\* cited by examiner

*Primary Examiner* — Kiet T Nguyen
(74) *Attorney, Agent, or Firm* — DLA Piper LLP (US)

(57) ABSTRACT

In a time-of-flight spectrum obtained when the overtaking of ions of different kinds has occurred, mass-to-charge ratios M1, M2, and M3 are computed with a predetermined conversion formula by using a plurality of assumed numbers of turns for one peak. Then, the flight times Tf1, Tf2, and Tf3 for an overtakingless measurement are computed by using an inverse conversion formula. If peaks respectively corresponding to the flight times Tf1, Tf2, and Tf3 for an overtakingless measurement exist on an overtakingless time-of-flight spectrum, their intensities i1, i2, and i3 are obtained. Then, the intensity Ia of the original peak is distributed to the mass-to-charge ratios M1, M2, and M3 in accordance with the intensity ratio. The same intensity distribution processing is performed for all or selected plural peaks. The intensities assigned to the same mass-to-charge ratio are integrated. A mass spectrum is created for each of a plurality of overtaking time-of-flight spectra obtained by changing the timing of deviation of ions from a loop orbit, and the plurality of mass spectra are displayed in a window of a display unit so that they can be compared. Thereby, the probability of missing an ion due to the ion deviation timing can be reduced.

10 Claims, 6 Drawing Sheets

Fig. 2

```
START
  ↓
S1: MEASURE THE MOLECULE WHOSE M/Z VALUE IS KNOWN, AND
    FROM THE RESULT, OBTAIN AN ACCURATE CONVERSION FORMULA
    BETWEEN THE FLIGHT TIME AND THE M/Z VALUE
  ↓
S2: ACTUALLY MEASURE THE SAMPLE TO BE MEASURED
    IN THE FIRST MEASUREMENT MODE (UNDER THE OVERTAKINGLESS
    TURNING CONDITIONS) TO OBTAIN AN OVERTAKINGLESS
    TIME-OF-FLIGHT SPECTRUM
  ↓
S3: ACTUALLY MEASURE THE SAMPLE TO BE MEASURED PLURAL TIMES
    IN THE SECOND MEASUREMENT MODE
    (UNDER THE OVERTAKING TURNING CONDITIONS)
    FOR DIFFERENT NUMBERS OF TURNS TO OBTAIN A PLURALITY OF
    OVERTAKING TIME-OF-FLIGHT SPECTRA
  ↓
S4: COMPUTE MASS SPECTRA BY PERFORMING AN INTENSITY DISTRIBUTION
    PROCESSING FOR EACH OF THE OVERTAKING TIME-OF-FLIGHT SPECTRA
    BY USING THE OVERTAKINGLESS TIME-OF-FLIGHT SPECTRUM
  ↓
S5: DISPLAY THE PLURALITY OF MASS SPECTRA
  ↓
END
```

Fig. 3

| ISOTOPE | ABUNDANCE RATIO [%] | m/z [Da] |
|---|---|---|
| 128Xe | 1.91 | 127.9035 |
| 129Xe | 26.4 | 128.9048 |
| 130Xe | 4.1 | 129.9035 |
| 131Xe | 21.29 | 130.9051 |
| 132Xe | 26.9 | 131.9042 |
| 134Xe | 10.4 | 133.9054 |
| 136Xe | 8.9 | 135.9072 |

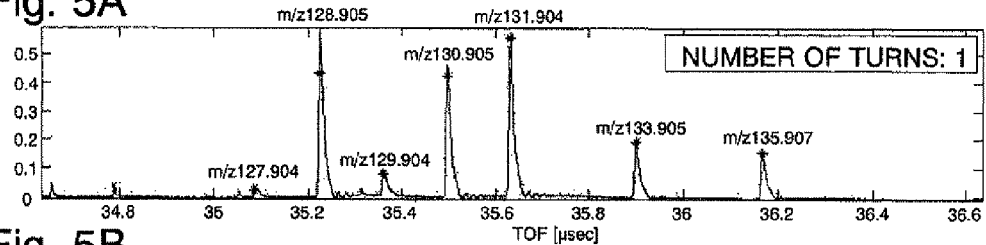
Fig. 5A
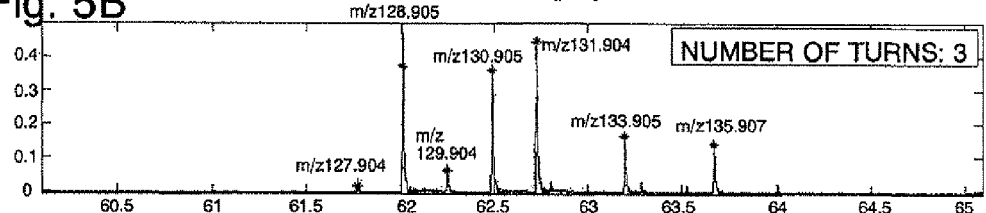
Fig. 5B
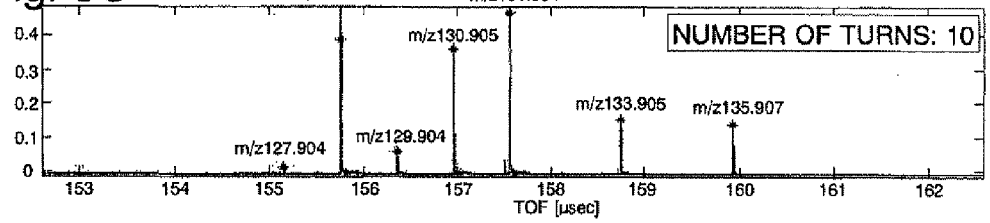
Fig. 5C
Fig. 6
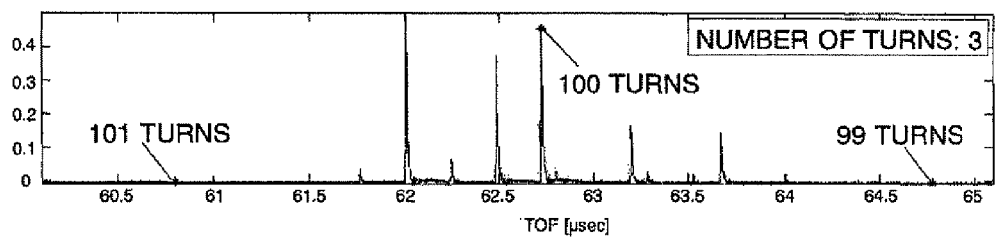

Fig. 7
| ISOTOPE | ACTUAL m/z | MEASURED m/z ALL UNITS: [Da] | |
|---|---|---|---|
| | | 100 TURNS | 300 TURNS |
| 128Xe | 127.9035 | 127.9071 | - |
| 129Xe | 128.9048 | - | 128.9079 |
| 130Xe | 129.9035 | 129.9068 | 129.9063 |
| 131Xe | 130.9051 | 130.9087 | 130.9081 |
| 132Xe | 131.9042 | 131.9077 | 131.9070 |
| 134Xe | 133.9054 | - | 133.9088 |
| 136Xe | 135.9072 | 135.9107 | 135.9102 |
Fig. 8
| ISOTOPE | ACTUAL m/z | CORRECTED VALUES OF MEASURED m/z ALL UNITS: [Da] | |
|---|---|---|---|
| | | 100 TURNS | 300 TURNS |
| 128Xe | 127.9035 | 127.9009 | - |
| 129Xe | 128.9048 | - | 128.9050 |
| 130Xe | 129.9035 | 129.9005 | 129.9033 |
| 131Xe | 130.9051 | 130.9022 | 130.9051 |
| 132Xe | 131.9042 | 131.9011 | 131.9040 |
| 134Xe | 133.9054 | - | 133.9057 |
| 136Xe | 135.9072 | 135.9040 | 135.9071 |
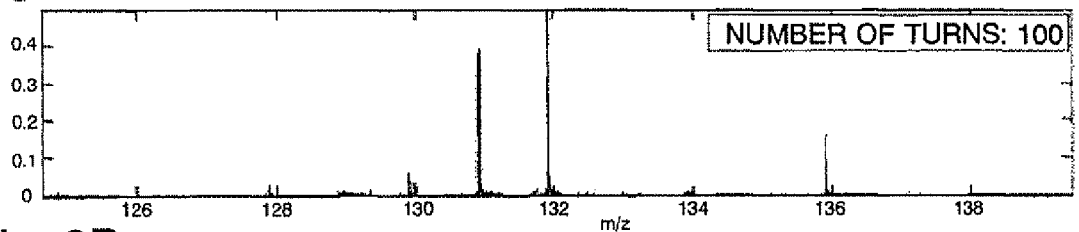
Fig. 9A
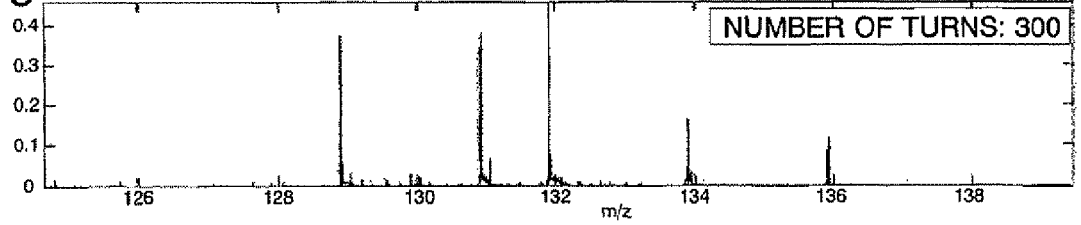
Fig. 9B Fig. 10A
OVERTAKING TIME-OF-FLIGHT SPECTRUM
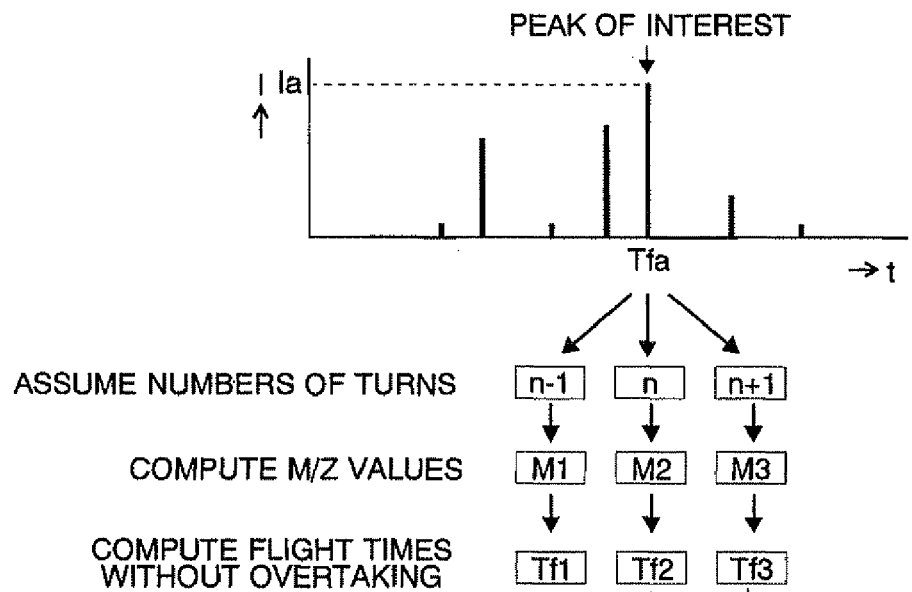
Fig. 10B
OVERTAKINGLESS TIME-OF-FLIGHT SPECTRUM
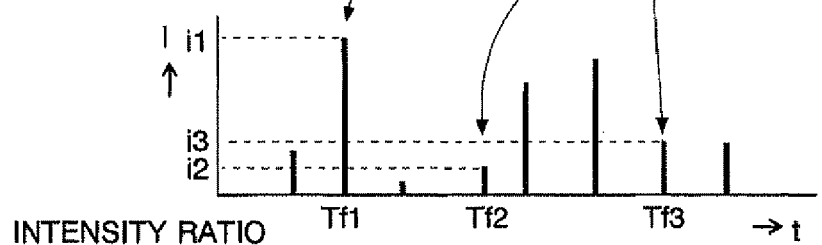
INTENSITY RATIO
OBTAIN THE INTENSITY RATIO OF THE PEAKS OF EACH FLIGHT TIME | INTENSITY RATIO i1 : i2 : i3
DISTRIBUTE THE INTENSITY Ia TO EACH M/Z VALUE ACCORDING TO THE INTENSITY RATIO
Fig. 10C MASS SPECTRUM
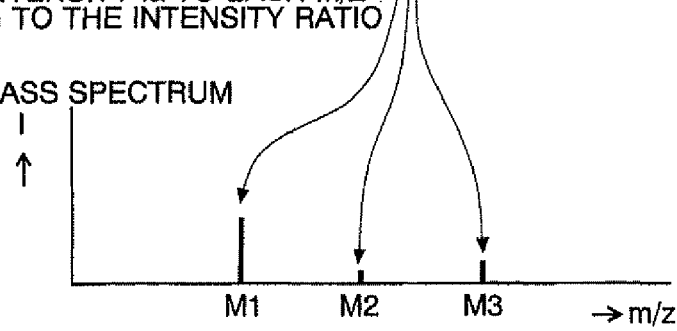

MASS-ANALYZING METHOD AND MASS SPECTROMETER

CROSS-REFERENCE TO THE RELATED APPLICATIONS

This application is a national stage of international application No. PCT/JP2008/003246, filed on Nov. 10, 2008, the entire contents of which are incorporated herein by reference.

TECHNICAL FIELD

The present invention relates to a multi-turn time-of-flight mass spectrometer in which ions originating from a sample are made to repeatedly fly along a closed loop orbit to separate and detect them in accordance with their mass-to-charge ratio (m/z). It also relates to a mass-analyzing method using the multi-turn time-of-flight mass spectrometer.

BACKGROUND ART

A "Time-of-Flight Mass Spectrometer" (hereinafter, TOFMS) is a type of device used for performing a mass analysis by measuring the time of flight required for each ion to travel a specific distance and converting the time of flight to the mass-to-charge ratio. This analysis is based on the principle that ions accelerated by a certain amount of energy will fly at different speeds corresponding to their mass-to-charge ratio. Accordingly, elongating the flight distance of ions is effective for enhancing the mass resolving power (or resolution of the mass-to-charge ratio m/z values). However, the elongation of a flight distance along a straight line requires an enlargement of the device. Given this factor, Multi-Turn Time-of-Flight Mass Spectrometers (Multi-Turn TOFMS; hereinafter, MT-TOFMS) have been developed in which ions are made to repeatedly fly along a closed orbit such as a substantially circular shape, substantially elliptical shape, substantially "8" figure shape, or other shapes, in order to simultaneously achieve the elongation of the flight distance and the downsizing of the apparatus (refer to Patent Documents 1 and 2, and other documents).

Another type of device developed for the same purpose is the multi-reflection time-of-flight mass analyzer, in which the aforementioned loop orbit is replaced by a reciprocative path in which a reflecting electric field is created to make ions fly back and forth multiple times and thereby elongate their flight distance. Although the multi-turn time-of-flight type and the multi-reflection time-of-flight type use different ion optical systems, they are essentially based on the same principle for improving the mass resolving power. Accordingly, in the context of the present description, the "multi-turn time-of-flight type" should be interpreted as inclusive of the "multi-reflection time-of-flight type."

As previously described, a MT-TOFMS can achieve a high level of mass resolving power. However, it has a drawback due to the fact that the flight path of the ions is a closed orbit. That is, as the number of turns of the ions increases, an ion having a smaller mass-to-charge ratio and flying faster overtakes another ion having a larger mass-to-charge ratio and flying at a lower speed. If such an overtaking of the ions having different mass-to-charge ratios occurs, it is possible that some of the peaks observed on an obtained time-of-flight spectrum correspond to multiple ions that have undergone a different number of turns, i.e. traveled different flight distances. This means it is no longer ensured that the mass-to-charge ratio and the time of flight uniquely correspond, so that the time-of-flight spectrum cannot be directly converted to a mass spectrum.

Because of the aforementioned drawback, in conventional MT-TOFMSs, ions are selected in advance among the ions that originate from a sample generated in an ion source so that their mass is limited to a range (i.e. range of mass-to-charge ratio m/z values) where the aforementioned overtaking will not occur. The selected ions are made to fly along the loop orbit to undergo a predetermined number of turns and then be detected. Although a mass spectrum with a high mass resolution can be obtained with such a method, the range of the mass spectrum is significantly limited. This is contrary to the advantage of TOFMSs that a mass spectrum with a relatively wide mass range can be obtained by one measurement.

Given this factor, a variety of methods have been conventionally proposed for deducing the number of turns of the peaks appearing on a time-of-flight spectrum in order to convert the time of flight to the mass-to-charge ratio. For example, Patent Document 3 proposes a method in which the results obtained by performing a plurality of mass analyses of the same sample under different conditions are compared to deduce the number of turns of the peaks appearing on a spectrum. Although such a method is effective, the data processing will be inevitably complicated. Moreover, the deduction of the number of turns is difficult particularly when the number of components contained in the sample is large.

Patent Document 4 proposes a method in which a multi-correlation function of plural time-of-flight spectra taken at different timings of deviation of ions from the loop orbit is computed to reconstruct a time-of-flight spectrum for a single turn. In this method, the following formula (1) is used to obtain the intensity G(T) of an ion with a flight time T on the loop orbit from plural sets of time-of-flight spectrum data obtained by performing a plurality of mass analyses under ejection timings that give different numbers of turns:

$$G(T) = \int_{yl}^{yu} H[F1\{N1(T) \times T + y\}, \quad (1)$$

$$F2\{N2(T) \times T + y\}, \ldots, Fr\{Nr(T) \times T + y\}] dy,$$

where Fj (j=1, 2, . . . , r) is the intensity of an ion with the number of turns Nj retrieved from the measurement data, y is the deviation of flight time, yl is the lower limit value of the deviation time, yu is the upper limit value of the deviation time, and H is a function determined by the values of the variables Fj. As specific examples of the function H, the arithmetic mean, the minimum value, the geometric mean, the harmonic mean, and other values are proposed. However, it is suggested that, in order to eliminate a pseudo peak which happens to have a large Fj value, the definition of the function H is preferably determined so that, among a variety of magnitudes of Fj, smaller values are more significantly reflected in the function H than larger values.

Patent Document 4 points out that, an insensitive period in which some ions travelling on the loop orbit are not detected may occur depending on the timing at which ions are ejected from the loop orbit. However, this document fails to propose any measures against it. This insensitive period occurs due to the fact that the gate electrode (ion mirror) for deviating ions from the loop orbit has a finite length and therefore an ion passing the gate electrode at the point in time when the turning ions are made to deviate is not ejected in an appropriate direction (i.e. the direction in which the ion can be detected by the detector). In the case where a processing is performed in accordance with H which is defined in such a manner as to lay weight on smaller values of Fj rather than larger values as previously described, in particular, in the case where the geometric mean or the harmonic mean is used, if any peak having an intensity of 0 is contained in peak intensities Fj, the peak will be excluded from the reconstructed time-of-flight spectrum. That is, the peaks of ions which are not observed in a plurality of mass analyses for different numbers of turns due to the insensitive period as previously described will not appear on the reconstructed spectrum. This may cause the failure of ion detection, resulting in the erroneous determination that a component that should be contained in the sample is not contained.

[Patent Document 1] JP-A 2006-228435
[Patent Document 2] JP-A 2008-27683
[Patent Document 3] JP-A 2005-116343
[Patent Document 4] JP-A 2005-79049

DISCLOSURE OF THE INVENTION

Problem to be Solved by the Invention

The present invention has been developed to solve the aforementioned problem, and the objective thereof is to provide a multi-turn time-of-flight mass spectrometer and mass-analyzing method capable of preventing an ion from being missed, by enabling, in the process of reconstructing a plurality of time-of-flight spectra obtained by a multi-turn method, the checking for the existence of ions which have not been properly detected due to the deviation timing from the loop orbit.

Means for Solving the Problem

To solve the aforementioned problem, the first aspect of the present invention provides a mass-analyzing method using a multi-turn time-of-flight mass spectrometer for making a variety of ions departing from an ion source fly along a loop orbit repeatedly plural times and then for introducing the ions into a detector to obtain a mass spectrum based on a detection signal, in which a conversion formula between a flight time and a mass-to-charge ratio is memorized, the conversion formula being obtained based on a result of an actual measurement of a flight time of an ion whose mass-to-charge ratio is previously known, the mass-analyzing method including the steps of:

a) a first measurement mode performing step for obtaining an overtakingless time-of-flight spectrum based on a detection signal obtained by the detector by performing a mass analysis of a sample to be measured in a first measurement mode in which ions are made to fly without multi-turning along the loop orbit or to multi-turn along the loop orbit until they undergo a specific number of turns which ensures that a catching or overtaking of different kinds of ions will not occur;

b) a second measurement mode performing step for performing a plurality of mass analyses of the sample to be measured while changing a timing of deviating ions from the loop orbit in such a manner that ions of a same kind undergo a different number of turns, each of the mass analyses being performed in a second measurement mode in which ions are deviated from the loop orbit and introduced into the detector at or after a predetermined point in time after they are made to multi-turn so that an overtaking of the ions will occur on the loop orbit, and for obtaining different overtaking time-of-flight spectra based on a detection signal provided from the detector; and c) a computation processing step for obtaining mass spectra respectively corresponding to the plurality of overtaking time-of-flight spectra by performing an intensity distribution processing in which: an assumed flight time without an overtaking is computed for each of peaks on each of the overtaking time-of-flight spectra obtained by performing the second measurement mode by using a plurality of assumed numbers of turns and the conversion formula; peaks respectively corresponding to the plurality of assumed flight times are identified on the overtakingless time-of-flight spectrum to obtain intensity information on the peaks; and intensities of original peaks on the overtaking time-of-flight spectrum are distributed, in accordance with the intensity information, to mass-to-charge ratios corresponding to the assumed flight times.

To solve the aforementioned problem, the second aspect of the present invention provides a multi-turn time-of-flight mass spectrometer, which is a mass spectrometer for realizing the mass-analyzing method according to the first aspect of the present invention, for making a variety of ions departing from an ion source fly along a loop orbit repeatedly plural times and then for introducing the ions into a detector to obtain a mass spectrum based on a detection signal, including:

a) a conversion information holding means for memorizing a conversion formula between a flight time and a mass-to-charge ratio, the conversion formula being obtained based on a result of an actual measurement of a flight time of an ion whose mass-to-charge ratio is previously known;

b) a first measurement mode performance controller for obtaining an overtakingless time-of-flight spectrum based on a detection signal obtained by a detector by performing a mass analysis of a sample to be measured in a first measurement mode in which ions are made to fly without multi-turning along the loop orbit or to multi-turn along the loop orbit until they undergo a specific number of turns which ensures that a catching or overtaking of different kinds of ions will not occur;

c) a second measurement mode performance controller for performing a plurality of mass analyses of the sample to be measured while changing a timing of deviating ions from the loop orbit in such a manner that ions of a same kind undergo a different number of turns, each of the mass analyses being performed in a second measurement mode in which ions are deviated from the loop orbit and introduced into the detector at or after a predetermined point in time after they are made to multi-turn so that an overtaking of the ions will occur on the loop orbit, and for obtaining different overtaking time-of-flight spectra based on a detection signal provided from the detector; and d) a computation processing means for obtaining mass spectra respectively corresponding to the plurality of overtaking time-of-flight spectra by performing an intensity distribution processing in which: an assumed flight time without an overtaking is computed for each of peaks on each of the overtaking time-of-flight spectra obtained by performing the second measurement mode by using a plurality of assumed numbers of turns and the conversion formula; peaks respectively corresponding to the plurality of assumed flight times are identified on the overtakingless time-of-flight spectrum to obtain intensity information on the peaks; and intensities of original peaks on the overtaking time-of-flight spectrum are distributed, in accordance with the intensity information, to mass-to-charge ratios corresponding to the assumed flight times.

In the mass-analyzing method according to the first aspect of the present invention and the mass spectrometer according to the second aspect of the present invention, when the first measurement mode is used, the catching and overtaking of different kinds of ions do not occur even when the ions are made to turn along the loop orbit. Therefore, the numbers of turns of ions corresponding to all the peaks appearing on the obtained overtakingless time-of-flight spectrum are the same. These peaks are aligned in the ascending order of mass-to-charge ratio. However, since their flight distance is not very long, the mass resolution and the mass accuracy are relatively low. On the other hand, in the second measurement mode, the overtaking of ions of different kinds occurs while they fly. Consequently, the numbers of turns of the ions corresponding to the peaks appearing on the obtained overtaking time-of-flight spectrum are not the same, and the arrangement of the peaks is not in the ascending order of their mass-to-charge ratio. However, since their flight distance can be elongated by increasing the number of turns, the mass resolution and the mass accuracy can be enhanced. Hence, based on an overtaking time-of-flight spectrum, it is possible to obtain a mass spectrum with a high mass resolution and high mass accuracy.

If the components in the sample to be measured are known to some extent or can be deduced, the mass-to-charge ratio (or the range of values that the mass-to-charge ratio can take) of the ion to be measured can be roughly known. From the timing of deviating ions from the loop orbit (i.e. the period of time from the point in time when a variety of ions depart from the ion source almost collectively until the point in time when the electric field is changed so that the variety of ions that have been introduced into the loop orbit leave the loop orbit) and the approximate mass-to-charge ratio of each ion in the second measurement mode, the number of turns of the ion in the second measurement mode can be roughly computed. Then, in the computation processing step (or the computation processing means), a plurality of possible numbers of turns of one peak in one overtaking time-of-flight spectrum are assumed around the number of turns obtained in the aforementioned manner. If one number of turns is assumed, the mass-to-charge ratio of the peak can be computed from the flight time of the peak by using the conversion formula. This mass-to-charge ratio, in turn, can be used to compute the flight time ("assumed flight time") on the overtakingless time-of-flight spectrum obtained in the first measurement mode.

The assumed flight time is obtained for each of the different assumed numbers of turns. Hence, from the overtakingless time-of-flight spectrum, peaks corresponding to the plurality of assumed flight times are identified and the intensity information of each peak is obtained. If a peak corresponding to the assumed flight time does not exit, the intensity thereof is set at zero. Ideally, peaks should exist only at flight times corresponding to the real numbers of turns out of the plurality of assumed numbers of turns. However, a peak might accidentally exist at a flight time corresponding to a false number of turns among the plurality of assumed numbers of turns. In such a case, i.e. in the case where peaks exist at a plurality of assumed flight times, the intensities of the original peaks on the overtaking time-of-flight spectrum are distributed, for example in accordance with the intensity ratio of the peaks, to the mass-to-charge ratios which have been converted from the assumed flight times. In the case where a peak exists only at the flight time corresponding to the true number of turns as previously described, all the intensity of the original peak on the overtaking time-of-flight spectrum is assigned to the single mass-to-charge ratio which is converted from the flight time.

In the computation processing step, the intensity distribution processing as previously described is performed for each of the plurality of peaks appearing on one overtaking time-of-flight spectrum, and the intensities distributed to the same mass-to-charge ratio on the mass spectrum are integrated. In this manner, one mass spectrum can be created from one overtaking time-of-flight spectrum. Consequently, mass spectra are respectively created from a plurality of overtaking time-of-flight spectra for different numbers of turns.

If an ion of a certain kind cannot be observed on one overtaking time-of-flight spectrum due to the aforementioned insensitive period, the peak of this missing ion does not appear on the mass spectrum created based on this time-of-flight spectrum. However, it is probable that the ion is observed in another overtaking time-of-flight spectrum which has been obtained under a different number of turns. That is, in the case where a plurality of overtaking time-of-flight spectra are obtained under the conditions of the timings of deviating ions for different numbers of turns, it is extremely unlikely that ions of one certain kind are not observed in any one of the plurality of overtaking time-of-flight spectra, As long as the ion is observed on any one of the overtaking time-of-flight spectra, the peak of the ion will assuredly appear on the mass spectrum obtained based on that spectrum. Therefore, by examining peaks appearing on the plurality of mass spectra, it is possible to know the accurate mass-to-charge ratios of all the components (molecules) contained in the sample to be measured without missing any of them.

In the case where a variety of impurities are contained in a minute amount in the measured sample, a large number of peaks originating from the impurities appear on the overtaking time-of-flight spectrum. In such a case, performing the intensity distribution processing for all the peaks in the overtaking time-of-flight spectrum complicates the mass spectrum and elongates the computation processing time. Hence, as an embodiment of the mass-analyzing method according to the first aspect of the present invention, it is preferable that, in the computation processing step, peaks appearing on the overtaking time-of-flight spectrum are selected in accordance with predetermined conditions, the intensity distribution processing is performed on the selected peaks, and the intensities distributed to the same mass-to-charge ratio on the mass spectrum are integrated. Examples of the conditions for selecting peaks include the selection of peaks whose intensity is equal to or larger than a threshold, the selection of a predetermined number of peaks in the descending order of their intensity, and other methods. Thereby, the time for computation processing can be saved, and the mass spectrum containing few unnecessary peaks can be obtained.

In the mass-analyzing method according to the first aspect of the present invention, it is preferable that, in the computation processing step, mass spectra are respectively obtained from the plurality of different overtaking time-of-flight spectra by the intensity distribution processing, and the plurality of mass spectra are shown on a same window of a display means. This enables a user to easily recognize a peak commonly appearing on the plurality of mass spectra, a peak which is observed on at least one of the mass spectra but is not observed on other mass spectra, and other information.

Effects of the Invention

With the mass-analyzing method according to the first aspect of the present invention and the mass spectrometer according to the second aspect of the present invention, it is possible to obtain a mass spectrum with a high mass resolving power and high mass accuracy based on a time-of-flight spectrum which is obtained by making ions repeatedly fly along a loop orbit multiple times in order to ensure a long flight time. What is more, all the target components contained in a sample to be measured can be assuredly detected. Thereby, it is possible to obtain the mass-to-charge ratio of the ion originating from the target component with a high mass resolving power and accuracy, while reducing the possibility of the detection failure of the target components.

BRIEF DESCRIPTION OF THE DRAWINGS

FIG. 2 is a flowchart showing an analysis procedure with the MT-TOFMS of the present embodiment.

FIG. 3 shows the abundance ratio and mass-to-charge ratio of Xe isotopic molecules.

FIGS. 5A through 5C show time-of-flight spectra deduced by using a flight time/mass-to-charge ratio conversion formula.

FIG. 6 shows a result of associating one peak on an overtaking time-of-flight spectrum for approximately 100 turns onto an overtakingless time-of-flight spectrum for approximately three turns.

FIG. 7 shows a result of converting the flight time to the mass-to-charge ratio based on the conversion formula obtained by using an overtakingless time-of-flight spectrum.

FIG. 8 shows a result of converting the flight time to the mass-to-charge ratio based on a conversion formula with enhanced accuracy by using a plurality of overtaking time-of-flight spectra.

FIGS. 9A and 9B show mass spectra obtained from the overtaking time-of-flight spectrum for approximately 100 turns and the overtaking time-of-flight spectrum for approximately 300 turns.

FIGS. 10A through 10C are schematic diagrams for showing a procedure of the intensity distribution processing for each of the peaks on an overtaking time-of-flight spectrum.

EXPLANATION OF NUMERALS

1 . . . Ion Source
2 . . . Gate Electrode
4 . . . Troidal Sector-Shaped Electrode
5 . . . Loop Orbit
6 . . . Injection Path
7 . . . Ejection Path
8 . . . Detector
9 . . . Data Processor
10 . . . Controller
11 . . . Injection/Ejection Voltage Generator
12 . . . Loop Flight Voltage Generator
13 . . . Input Unit
14 . . . Display Unit

BEST MODE FOR CARRYING OUT THE INVENTION

Figure 1:
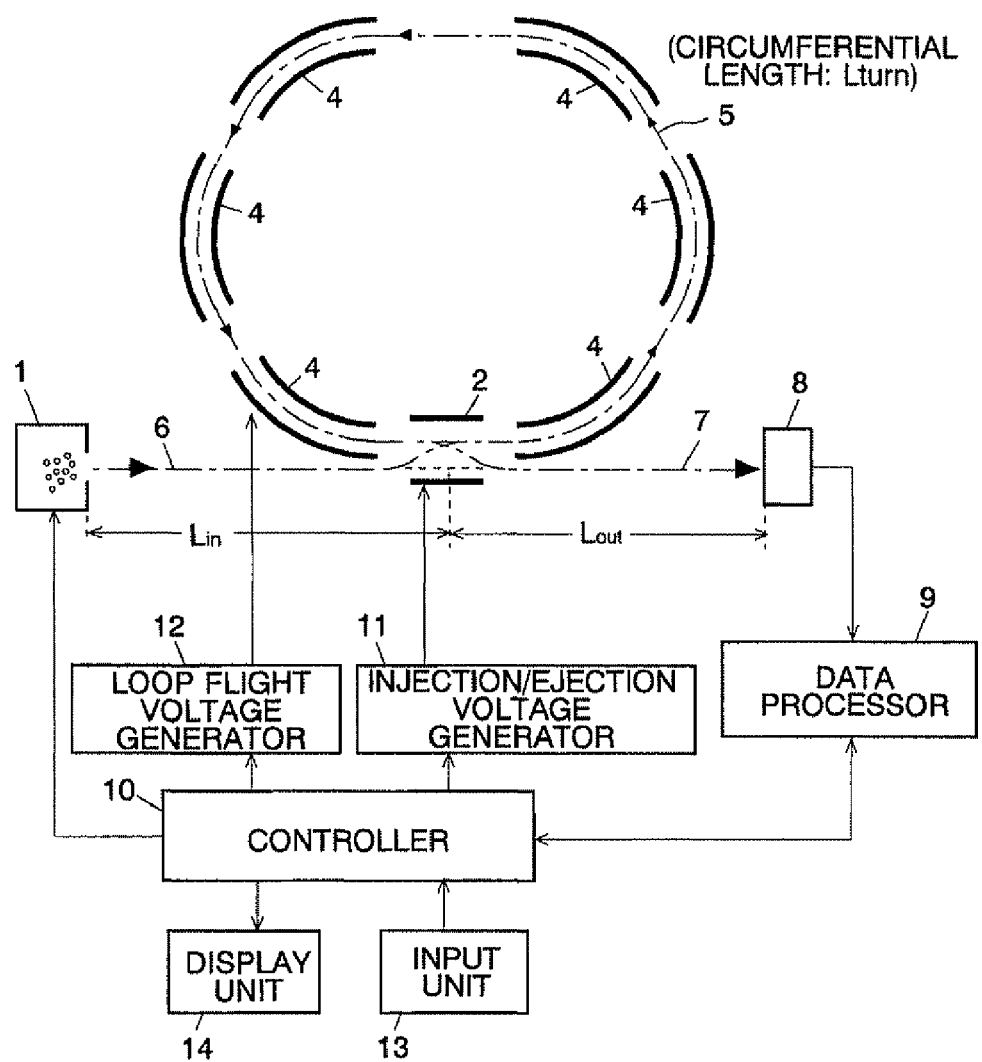
FIG. 1 is a schematic configuration diagram of an MT-TOFMS according to an embodiment of the present invention.

The MT-TOFMS which is an embodiment of the present invention will be described with reference to the attached figures. FIG. 1 is a schematic configuration diagram of the MT-TOFMS of the present embodiment.

In an ion source 1, sample molecules are ionized, and a predetermined energy is given to a variety of generated ions so that they start flying. Alternatively, the ion source 1 may temporarily store ions generated outside and collectively give an energy to the ions so as to make them start flying, like a three-dimensional quadrupole ion trap for example.

Ions which have started flying from the ion source 1 as a starting point are introduced into a loop orbit 5 through a deflection electric field formed by a gate electrode 2. The loop orbit 5 is formed by the action of electric fields respectively generated by a plurality of troidal sector-shaped electrodes 4. The shape of the loop orbit 5 is not limited to this type; it can be any shape, such as an "8" figured shape. Further, it does not necessarily have to be a completely closed orbit; it may be a linear or curved reciprocative orbit or a helical orbit having a gradually-shifting orbit.

After completing one or more turns along the loop orbit 5, the ions are deviated (or ejected) from the loop orbit 5 through the deflection electric field formed by the gate electrode 2, and reach, and detected by, a detector 8 which is provided outside. In this example, the gate electrode 2 doubles as the electrode for introducing ions into the loop orbit 5 and the electrode for deviating ions from the loop orbit 5. However, separate electrodes may be provided, or a part of the sector-shaped electrode 4 may be used instead of the gate electrode 2.

The detection signal by the detector 8 is provided to a data processor 9, where the flight times from the point in time when ions depart from the ion source 1 until the point in time when they finally reach the detector 8 are measured to create a time-of-flight spectrum. In addition, by performing a data analysis processing as will be described later, a mass spectrum is created from the time-of-flight spectrum. An injection/ejection voltage generator 11 applies, to the gate electrode 2 at a predetermined timing, a deflection voltage for introducing ions into the loop orbit 5 and a deflection voltage for deviating ions from the loop orbit 5. A loop flight voltage generator 12 generates a sector-shaped electric field by applying a predetermined voltage to each of the plurality of sector-shaped electrodes 4. Each of the voltage generators 11 and 12 and the ion source 1 operates under the control of a controller 10. Connected to the controller 10 are an input unit 13 for allowing a user to enter a variety of parameters for analysis and a display unit 14 for displaying analysis results such as a mass spectrum.

In FIG. 1, an injection path 6 is the flight path of ions from the ion source 1 to the loop orbit 5, and has a length of Lin. An ejection path 7 is the flight path of ions from the ion ejection point of loop orbit 5 to the detector 8, and has a length of Lout, The flight length of one turn, i.e. circumferential length, of the loop orbit 5 is Lturn.

In the MT-TOFMS of the present embodiment, a variety of ions ejected from the ion source 1 pass the injection path 6, and are introduced into the loop orbit 5 through the gate electrode 2, which is controlled by the injection/ejection flight voltage generator 11. Then, the ions fly along the loop orbit 5 completing one or more turns in accordance with the sector-shaped electric fields formed by sector-shaped electrodes 4 controlled by the loop flight voltage generator 12. Although the variety of ions are ejected from the ion source 1 almost simultaneously, since ions having a smaller mass-to-charge ratio fly faster, the intervals between ions having different mass-to-charge ratios increase as the number of turns of ions increases. When the voltage applied to the gate electrode 2 from the injection/ejection flight voltage generator 11 is changed to the voltage for deviating ions while the ions are flying on the loop orbit 5, they deviate from the loop orbit 5 in the order of reaching the gate electrode 2 and reach the detector 8 through the ejection path 7.

Since the loop orbit 5 is closed, as the number of turns of ions increases, at a certain point in time, an ion having a small mass-to-charge ratio and flying at the highest speed catches and overtakes an ion having a large mass-to-charge ratio and flying at the lowest speed. Until that point in time, by changing the voltage applied to the gate electrode 2 to the deviation voltage from the point in time when the ion flying at the lowest speed passes the gate electrode 2 until the ion flying at the highest speed reaches the gate electrode 2, it is possible to deviate ions in the ascending order of their mass-to-charge ratio to make them reach the detector 8. The measurement mode which ensures this operation is the first measurement mode, and a time-of-flight spectrum obtained in the first measurement mode is called an overtakingless time-of-flight spectrum. In this case, all the ions corresponding to the peaks appearing on the time-of-flight spectrum undergo the same number of turns.

Meanwhile, if an overtaking of ions of even one kind occurs on the loop orbit 5, after that point in time, ions will no longer reach the detector 8 in the ascending order of their mass-to-charge ratio. This measurement mode is the second measurement mode, and a time-of-flight spectrum obtained in the second measurement mode is called an overtaking time-of-flight spectrum. In this case, the ions corresponding to the peaks appearing on the time-of-flight spectrum do not undergo the same number of turns, and the numbers of turns of ions which have been lapped are relatively small. However, since the mass resolving power depends on the flight distance, i.e. the number of turns, the mass resolving power enhances as the number of turns increases. Therefore, in order to compute an accurate mass-to-charge ratio, it is necessary to obtain a mass spectrum not from an overtakingless time-of-flight spectrum but from an overtaking time-of-flight spectrum. To this end, in the MT-TOFMS of the present embodiment, a characterizing measurement and data processing are performed, which will be described using a concrete example with reference to FIGS. 2 through 10C.

As an example, consider the ease where the mass-to-charge ratio of isotopic molecules of xenon (Xe) is measured. The abundance ratio and the mass-to-charge ratio (m/z) of the isotopic molecules of xenon (Xe) are shown in FIG. 3.

FIGS. 4A through 4E show time-of-flight spectra obtained by measuring the isotopic molecules of xenon listed in FIG. 3 with the aforementioned MT-TOFMS. FIGS. 4A through 4E show the time-of-flight spectra in which the number of turns has been respectively set at 1, 3, 10, 100, and 300. However, the number of turns of each peak on the time-of-flight spectrum is practically unknown, and their number of turns is not the same if a lapping as previously described occurs. Therefore, those aforementioned set numbers of turns are merely a rough indication.

The relationship between the flight time Tf and the mass-to-charge ratio m/z of an ion in an MT-TOFMS is given by the following theoretical formula (2):

$$m/z = \frac{(L_{in} + L_{out} + nL_{turn})^2}{2V_0(e/u)} Tf^2, \quad (2)$$

where u denotes the atomic mass [kg], e denotes the elementary charge [C], $V_0$ denotes the ion acceleration voltage [V], and n denotes the number of turns of the ion. Lin, Lout, and Lturn are the aforementioned distances [m], which are known because they are determined by the geometric arrangement of the ion optical components. Generally, $V_0$ is an intrinsic value of the apparatus, which is also known. Therefore, only Tf and m/z are unknown values in the formula (2).

Given that the number of turns of 128Xe having the smallest mass-to-charge ratio m/z and that of 136Xe having the largest mass-to-charge ratio m/z in FIG. 3 are the same (i.e. an overtaking of ions does not occur during their flight), the following formula (3) holds from the formula (2), letting the electric charge z be 1:

$$\{L^{in}+L^{out}+(n+1)L^{turn}\}\sqrt{m^1}=(L^{in}+L^{out}+nL^{turn})\sqrt{m^2} \quad (3)$$

where m1 is the mass-to-charge ratio of the 128Xe, and m2 is the mass-to-charge ratio of the 136Xe. For example, calculating the number n of turns from the formula (3) with Lin=1.01344[m], Lout=0.53502[m] and Lturn=0.97364[m] will show that the isotopic molecules of Xe can be measured without an overtaking when the number of turns is less than or equal to 30. That is, in FIGS. 4A through 4E, 4A through 4C are overtakingless time-of-flight spectra, and 4D and 4E are overtaking time-of-flight spectra.

Obtaining a mass spectrum from an overtaking time-of-flight spectrum in the MS-TOFMS of the present embodiment requires the conversion formula (2). A theoretical conversion formula as described earlier may be used without change. However, in an actual apparatus, there is a variation because ions do not always fly along the orbit as planned (or center orbit) or for other reasons. Hence, in the MT-TOFMS of the present embodiment, molecules whose mass-to-charge ratio is previously known are actually measured, and by using the result of the actual measurement, an accurate conversion formula for mutually converting the flight time and the mass-to-charge ratio is obtained, which is memorized inside the data processor 9 (Step S1). Here, as an example, the conversion formula is obtained by using the method disclosed in JP-A 2005-322429.

That is, initially, using an overtakingless time-of-flight spectrum obtained by an actual measurement of isotopic molecules of Xe whose mass-to-charge ratio is known, two parameters of Loff and $V_0$ in the modified conversion formula, the following formula (4), are deduced:

$$m/z = \frac{(L_{in} + L_{out} + L_{off} + nL_{turn})^2}{2V_0(e/u)} Tf^2. \quad (4)$$

Figure 4A:
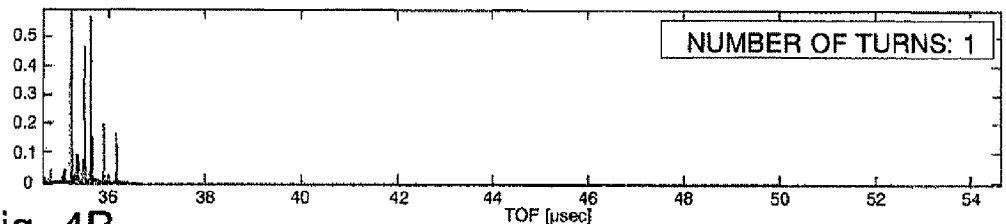
FIGS. 4A through 4E show time-of-flight spectra obtained by measuring Xe isotopic molecules with the MT-TOFMS of the present embodiment.
Figure 4B:
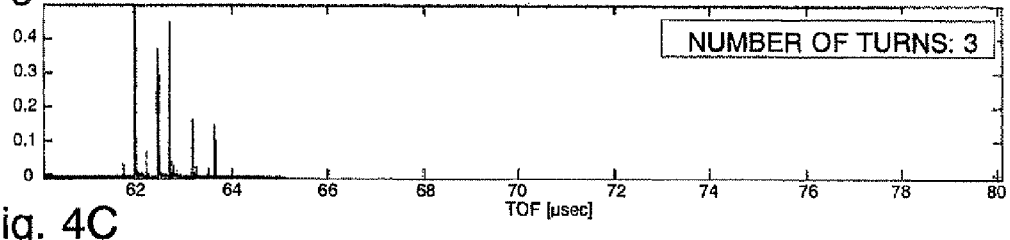
Figure 4C:
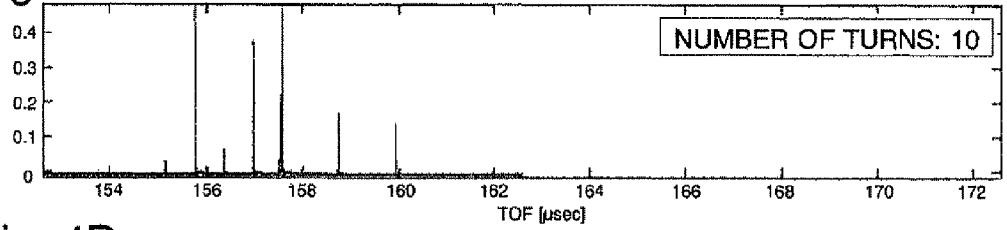

As previously described, FIGS. 4A, 4B, and 4C are overtakingless time-of-flight spectra. Hence, by using these spectra, the measurement value of Tf of the isotopic molecules of Xe is obtained. Then, the parameters Loff and $V_0$ are deduced in such a manner as to minimize the error between the computed value of Tf which is obtained by converting the accurate mass-to-charge ratio m/z shown in FIG. 3 using the formula (2) and the measurement value of Tf based on the actual measurement. As shown in FIGS. 5A through 5C, the flight times deduced by using the modified conversion formula obtained as previously described approximately matched the flight times of peaks on actually measured time-of-flight spectra. Based on this result, the conversion formula from the flight time Tf to the mass-to-charge ratio m/z can be obtained. Of course, an inverse conversion from the mass-to-charge ratio m/z to the flight time can be performed by using the following inverse conversion formula (5), which is obtained by transforming the formula (4):

$$Tf = \frac{\sqrt{2V_0(e/u)}}{L_{in} + L_{out} + L_{off} + nL_{turn}} \sqrt{m/z}. \quad (5)$$

Next, in the overtaking time-of-flight spectra (FIGS. 4D and 4E), in which the overtaking of ions has occurred, the number of turns of the isotopic molecules of Xe is deduced.

To this end, the flight times of the peaks in the overtaking time-of-flight spectrum data are converted to the mass-to-charge ratios m/z by applying the formula (4) after assuming the number n of turns. Then, the mass-to-charge ratios m/z are converted, by using the formula (5), to the flight times based on the data of the known number $n_0$ of turns, and the ion intensities $Pn_0(n)$ are examined in the overtakingless time-of-flight spectrum. After that, some $Pn_0(n)$ obtained by assuming different numbers n of turns are compared, and the value of n that gives the largest $Pn_0(n)$ is assumed to be the real number of turns.

Figure 4D:
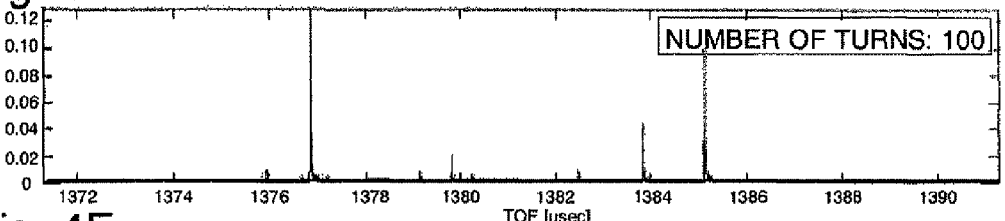

As an example, FIG. 6 shows a result of an examination of the ion intensity $Pn_0(n)$ on the three-turn time-of-flight spectrum (FIG. 4B) of the peak of 1376.8522 [µs] on the approximately 100-turn time-of-flight spectrum (FIG. 4D). The computed values of Tf with the assumption that their numbers of turns were 99, 100, and 101 are included in the range of the measurement value of Tf obtained by an actual measurement. The ion intensity $Pn_0(n)$ is largest at the number of turns of 100. Hence, let n=100 be the true number of turns to be obtained. In this manner, the overtaking time-of-flight spectrum data obtained by multi-turn mass analyzing isotopic molecular ions of Xe whose mass-to-charge ratio was known was used to obtain the number of turns of the ions, and the measurement value of Tf was converted to the mass-to-charge ratio m/z. The result is shown in FIG. 7. The "–" mark in FIG. 7 means that the molecule concerned was not observed.

Further, by using the result of FIG. 7, Loff and $V_0$ in formulas (4) and (5) are deduced for each actually-measured overtaking time-of-flight spectrum. That is, as opposed to the previously described case where Loff and $V_0$ were deduced by using only the result of an actual measurement of an overtakingless time-of-flight spectrum, the deduction in the present case is performed additionally including the result of an actual measurement of an overtaking time-of-flight spectrum for a longer flight time (a larger number of turns). This further enhances the accuracy of the conversion between the measurement value of Tf and the mass-to-charge ratio m/z. FIG. 8 shows the conversion result based on the remodified conversion formula as just described. It is understood that the values are closer to the actual mass-to-charge ratios m/z compared to the result of FIG. 7. In this manner, a more accurate conversion formula can be obtained. The processing of obtaining such a conversion formula does not have to be performed immediately before the measurement of the sample; it is possible perform the processing may at any appropriate point in time to obtain the conversion formula and memorize the formula beforehand.

In performing a measurement of an unknown sample, first, a mass analysis of the sample is performed in the first measurement mode, i.e. under the conditions which ensure that the overtaking of ions of different kinds will not occur, to obtain an overtakingless time-of-flight spectrum (Step S2).

In the case where the components contained in the sample to be measured are completely unknown, a variety of ions departing from the ion source 1 may be introduced into the detector 8 while bypassing a turn along the loop orbit 5. In the configuration of FIG. 1, the variety of ions are made to fly straight to pass the loop orbit 5 by not applying a deflection voltage to the gate electrode 2, so that ions are directly introduced into the ejection path 7 from the injection path 6 to bypass the loop orbit 5. In the case where the components contained in the sample to be measured can be deduced and it is certain that the catching and overtaking of ions will not occur after the ions undergo one turn or a small number of turns on the loop orbit, the ions may be allowed to complete that number of turns. For example, in the aforementioned example, in the case where 128Xe is the ion having the smallest mass-to-charge ratio among the components which might be contained and 136Xe is the ion having the largest mass-to-charge ratio among the components which might be contained, up to 29 turns (actually, the time corresponding to that number of turns) can be allowed.

Next, in Step S3, a mass analysis of the same sample in the second measurement mode is repeated plural times to obtain an overtaking time-of-flight spectrum for each analysis. These analyses are performed with different periods of time from the point in time when a variety of ions depart from the ion source 1 until the point in time when the voltage applied to the gate electrode 2 is changed so that the ions on the loop orbit 5 are deviated from the loop orbit 5 to be directed to the detector 8. In the obtained overtaking time-of-flight spectrum, peaks are not arranged in the ascending order of their mass-to-charge ratio because the overtaking of ions of different kinds has occurred. In addition, as already explained, the numbers of turns of peaks are not the same.

Hence, it is necessary to deduce the number of turns of each peak to obtain a mass spectrum from the overtaking time-of-flight spectrum. Similar to the previously described process, this deduction process also includes assuming the number of turns to obtain the flight time, identifying the peak corresponding to the flight time on the overtakingless time-of-flight spectrum, and utilizing the intensity of the identified peak. However, there is a difference as follows: In the previously described processing of Step S1, if a plurality of numbers of turns can be assumed for associating a peak observed on an overtaking time-of-flight spectrum with overtakingless time-of-flight spectrum data, the number of turns which corresponds to the peak that gives the highest ion intensity is considered to be the true number of turns. On the other hand, in the present process aimed at obtaining a mass spectrum, the intensities of the peaks on the overtaking time-of-flight spectrum are distributed to a plurality of mass-to-charge ratios in accordance with the ion intensities corresponding to a plurality of assumed numbers of turns (Step S4). This processing is called an intensity distribution processing, which will be described with reference to FIGS. 10A through 10C.

Consider the case where the overtaking time-of-flight spectrum shown in FIG. 10A was obtained under the conditions where a certain ion deviation timing was set. As previously described, the number of turns of each peak appearing on the overtaking time-of-flight spectrum is unknown. Here, consider one peak on the time-of-flight spectrum. The flight time of this peak is Tfa, and its peak intensity is Ia. Since its number of turns is unknown, the number of turns is assumed in a possible range and then the mass-to-charge ratio is obtained from the flight time Tfa. If there are three possible numbers of turns of n−1, n, and n+1, the mass-to-charge ratio can be computed for each of these assumed numbers of turns by using the previously memorized conversion formula. Assume that the computed mass-to-charge ratios were M1, M2, and M3, respectively corresponding to the numbers of turns of n−1, n, and n+1. Each of the mass-to-charge ratios can be converted to the flight time in the overtakingless measurement by using a previously memorized inverse conversion formula. Hence, from the mass-to-charge ratios M1, M2, and M3, the flight times Tf1, Tf2, and Tf3 are computed.

Subsequently, on the overtakingless time-of-flight spectrum obtained by an actual measurement of the sample in Step S2, the peaks corresponding to the aforementioned assumed flight times Tf1, Tf2, and Tf3 are located. In this example, consider the case where the corresponding peaks were found on the overtakingless time-of-flight spectrum as shown in FIG. 10B. However, a peak does not always exist for every assumed flight time. If such a peak does not exist, the intensity can be set at zero. After a plurality of peaks are found as shown in FIG. 10B, the intensities i1, i2, and i3 of the peaks are obtained, and then their intensity ratio is obtained. After that, the intensity Ia of the peak of interest is distributed to the mass-to-charge ratios M1, M2 and M3, in accordance with the intensity ratio of the aforementioned peaks.

That is, $Ia \times \{i1/(i1+i2\pm i3)\}$ is distributed to m/z=M1, $Ia \times \{i2/(i1+i2+i3)\}$ to m/z=M2, and $Ia \times \{i3/(i1+i2+i3)\}$ to m/z=M3. Then, as shown in FIG. 10C, the distributed intensities are recorded on the mass spectrum. In the case where a peak is found at only one of the assumed flight times on the overtakingless time-of-flight spectrum, the intensity Ia of the original peak of interest may be assigned to the mass-to-charge ratio that corresponds to that single assumed flight time, regardless of the intensity of the peak.

By the previously described procedure, the intensity of one peak on one overtaking time-of-flight spectrum can be reflected to the peak intensity of one or more mass-to-charge ratios on the mass spectrum. The same intensity distribution processing is repeated for each peak on one overtaking time-of-flight spectrum to distribute the peak intensity on one mass spectrum. When intensities are distributed to the same mass-to-charge ratio, these intensities will be integrated. Consequently, one mass spectrum is finally created from one overtaking time-of-flight spectrum. Since the intensities on the mass spectrum are relative, the integrated values may be finally normalized. The same operation is performed fdr each of the plurality of the time-of-flight spectra obtained in Step S3 to create different mass spectra. Hence, the number of the mass spectra created in the processing of Step S4 is the same as the number of overtaking time-of-flight spectra obtained in Step S3.

In the case where a huge number of peaks appear on one overtaking time-of-flight spectrum, performing the intensity distribution processing for all the peaks takes a long computation processing time. In addition, in such a case, most peaks having a small intensity originate from impurities mixed in the measured sample. Hence, performing the intensity distribution processing for all the peaks complicates the mass spectrum. Given these factors, a peak selection processing may be performed for the peaks appearing on the overtaking time-of-flight spectrum to select peaks whose intensity is equal to or higher than a threshold for example. In this case, the intensity distribution processing is performed to only the selected peaks.

In the example shown in FIG. 6, 0.83%, 98.6%, and 0.57% of the intensity of the peak of 1376.8522 [µs] in the overtaking time-of-flight spectrum for about 100 turns are respectively assigned to m/z=123.9449 (flight time of 60.8034 [µs] in the overtakingless time-of-flight spectrum for three turns), m/z=131.9062 (flight time of 62.7258 [µs] in the overtakingless time-of-flight spectrum for three turns), and m/z=140.6595 (flight time of 64.7736 [µs] in the overtakingless time-of-flight spectrum for three turns).

When a plurality of mass spectra are obtained in the previously described manner, the controller 10 displays the plurality of mass spectra on the same window of the display unit 14 (Step S5). In this step, the plurality of mass spectra may be displayed side by side, or may be superimposed with different line colors on the same m/z value axis.

Figure 4E:
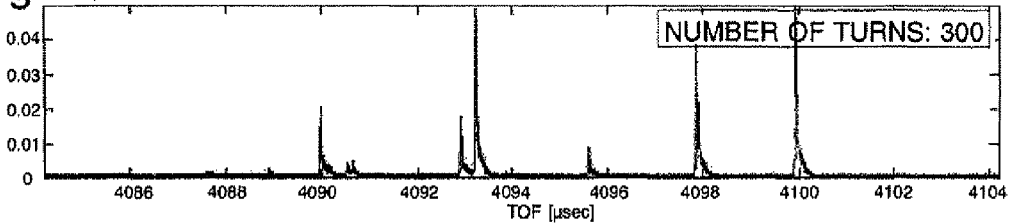

FIGS. 9A and 9B respectively show the mass spectra obtained by associating the overtaking time-of-flight spectrum for approximately 100 turns shown in FIG. 4D and the overtaking time-of-flight spectrum for approximately 300 turns shown in FIG. 4E with the overtakingless time-of-flight spectrum shown in FIG. 4C. By comparing these two mass spectra, it is understood that $^{130}Xe$, $^{131}Xe$, $^{132}Xe$, and $^{136}Xe$ are observed in both mass spectra. However, $^{128}Xe$, $^{129}Xe$, and $^{134}Xe$ are each observed only on one mass spectrum and not on the other. Therefore, it can be assumed that the ions of the latter three kinds of isotopic molecules failed to be detected due to the aforementioned insensitive period.

As just described, with the MT-TOMFS of the present embodiment, even ions which have not been properly detected due to the timing of the deviation of ions from the loop orbit 5 can be recognized, and their mass-to-charge ratios can be obtained with a high resolving power and accuracy. Of course, the larger the number of overtaking time-of-flight spectra obtained in the second measurement mode is, the lower the probability of detection failure of ions becomes. Hence, the number of times of executing the second measurement mode may be determined in an allowable measurement time.

It should be noted that the embodiment described thus far is merely an example of the present invention, and it is evident that any modification, adjustment, or addition appropriately made within the spirit of the present invention is also included in the scope of the claims of the present application.

The invention claimed is:

1. A mass-analyzing method using a multi-turn time-of-flight mass spectrometer for making a variety of ions departing from an ion source fly along a loop orbit repeatedly plural times and then for introducing the ions into a detector to obtain a mass spectrum based on a detection signal, in which a conversion formula between a flight time and a mass-to-charge ratio is memorized, the conversion formula being obtained based on a result of an actual measurement of a flight time of an ion whose mass-to-charge ratio is previously known, the mass-analyzing method comprising the steps of:
    a) a first measurement mode performing step for obtaining an overtakingless time-of-flight spectrum based on a detection signal obtained by a detector by performing a mass analysis of a sample to be measured in a first measurement mode in which ions are made to fly without multi-turning along the loop orbit or to multi-turn along the loop orbit until they undergo a specific number of turns which ensures that a catching or overtaking of different kinds of ions will not occur;
    b) a second measurement mode performing step for performing a plurality of mass analyses of the sample to be measured while changing a timing of deviating ions from the loop orbit in such a manner that ions of a same kind undergo a different number of turns, each of the mass analyses being performed in a second measurement mode in which ions are deviated from the loop orbit and introduced into the detector at or after a predetermined point in time after they are made to multi-turn so that an overtaking of the ions will occur on the loop orbit, and for obtaining different overtaking time-of-flight spectra based on a detection signal provided from the detector; and
    c) a computation processing step for obtaining mass spectra respectively corresponding to the plurality of overtaking time-of-flight spectra by performing an intensity distribution processing in which: an assumed flight time without an overtaking is computed for each of peaks on each of the overtaking time-of-flight spectra obtained by performing the second measurement mode by using a plurality of assumed numbers of turns and the conversion formula; peaks respectively corresponding to the plurality of assumed flight times are identified on the overtakingless time-of-flight spectrum to obtain intensity information on the peaks; and intensities of original peaks on the overtaking time-of-flight spectrum are distributed, in accordance with the intensity information, to mass-to-charge ratios corresponding to the assumed flight times.

2. The mass-analyzing method according to claim 1, wherein:
in the computation processing step, the intensity distribution processing is performed for each of the plurality of peaks appearing on the overtaking time-of-flight spectrum and the intensities distributed to a same mass-to-charge ratio on the mass spectrum are integrated.

3. The mass-analyzing method according to claim 2, wherein:
in the computation processing step, peaks appearing on the overtaking time-of-flight spectrum are selected in accordance with predetermined conditions, the intensity distribution processing is performed on the selected peaks, and the intensities distributed to the same mass-to-charge ratio on the mass spectrum are integrated.

4. The mass-analyzing method according to claim 3, wherein:
in the computation processing step, mass spectra are respectively obtained from the plurality of different overtaking time-of-flight spectra by the intensity distribution processing, and the plurality of mass spectra are shown on a same window of a display means.

5. The mass-analyzing method according to claim 2, wherein:
in the computation processing step, mass spectra are respectively obtained from the plurality of different overtaking time-of-flight spectra by the intensity distribution processing, and the plurality of mass spectra are shown on a same window of a display means.

6. A multi-turn time-of-flight mass spectrometer for making a variety of ions departing from an ion source fly along a loop orbit repeatedly plural times and then for introducing the ions into a detector to obtain a mass spectrum based on a detection signal, comprising:
a) a conversion information holding means for memorizing a conversion formula between a flight time and a mass-to-charge ratio, the conversion formula being obtained based on a result of an actual measurement of a flight time of an ion whose mass-to-charge ratio is previously known;
b) a first measurement mode performance controller for obtaining an overtakingless time-of-flight spectrum based on a detection signal obtained by a detector by performing a mass analysis of a sample to be measured in a first measurement mode in which ions are made to fly without multi-turning along the loop orbit or to multi-turn along the loop orbit until they undergo a specific number of turns which ensures that a catching or overtaking of different kinds of ions will not occur;
c) a second measurement mode performance controller for performing a plurality of mass analyses of the sample to be measured while changing a timing of deviating ions from the loop orbit in such a manner that ions of a same kind undergo a different number of turns, each of the mass analyses being performed in a second measurement mode in which ions are deviated from the loop orbit and introduced into the detector at or after a predetermined point in time after they are made to multi-turn so that an overtaking of the ions will occur on the loop orbit, and for obtaining different overtaking time-of-flight spectra based on a detection signal provided from the detector; and
d) a computation processing means for obtaining mass spectra respectively corresponding to the plurality of overtaking time-of-flight spectra by performing an intensity distribution processing in which: an assumed flight time without an overtaking is computed for each of peaks on each of the overtaking time-of-flight spectra obtained by performing the second measurement mode by using a plurality of assumed numbers of turns and the conversion formula;
peaks respectively corresponding to the plurality of assumed flight times are identified on the overtakingless time-of-flight spectrum to obtain intensity information on the peaks; and intensities of original peaks on the overtaking time-of-flight spectrum are distributed, in accordance with the intensity information, to mass-to-charge ratios corresponding to the assumed flight times.

7. The mass spectrometer according to claim 6, wherein:
the computation processing means performs the intensity distribution processing for each of the plurality of peaks appearing on the overtaking time-of-flight spectrum and integrates the intensities distributed to a same mass-to-charge ratio on the mass spectrum.

8. The mass spectrometer according to claim 7, wherein:
the computation processing means includes a peak selector for selecting peaks appearing on the overtaking time-of-flight spectrum in accordance with predetermined conditions, performs the intensity distribution processing on the selected peaks, and integrates the intensities distributed to the same mass-to-charge ratio on the mass spectrum.

9. The mass spectrometer according to claim 8, wherein:
the computation processing means respectively obtains mass spectra from the plurality of different overtaking time-of-flight spectra by the intensity distribution processing, and shows the plurality of mass spectra on a same window of a display means.

10. The mass spectrometer according to claim 7, wherein:
the computation processing means respectively obtains mass spectra from the plurality of different overtaking time-of-flight spectra by the intensity distribution processing, and shows the plurality of mass spectra on a same window of a display means.

* * * * *